United States Patent [19]

Israel

[11] Patent Number: 5,318,898
[45] Date of Patent: Jun. 7, 1994

[54] PRODUCTION OF RECOMBINANT BONE-INDUCING PROTEINS

[75] Inventor: David I. Israel, Concord, Mass.

[73] Assignee: Genetics Institute, Inc., Cambridge, Mass.

[21] Appl. No.: 679,451

[22] Filed: Apr. 2, 1991

[51] Int. Cl.$^5$ .................. C12P 21/00; C12P 21/02; C12N 5/02; C12N 5/10
[52] U.S. Cl. ..................... 435/69.1; 435/70.3; 435/240.2; 435/240.3
[58] Field of Search ............... 435/69.1, 70.3, 240.2, 435/240.3

[56] References Cited

U.S. PATENT DOCUMENTS 3,407,076  10/1968  Ganz ........................... 530/360
4,994,387   2/1991  Levine et al. .

OTHER PUBLICATIONS

Matsuoka, et al. Effects of Dextran Sulfate on Stabilization of Milk Lipoprotein Lipose and VLDL Triglycerine Hydrolysis in vitro Tohoku J. Exp. Medicine, vol. 149, pp. 61–66 1986.
Wang, et al. Recombinant Human Bone Morphogenetic Protein Induces Bone Formation, Proc. Natl. Acad. Sci. USA, vol. 87, pp. 2220–2224, Mar. 1990.
Wozney, John M. et al., Science 242:1528–1534 (1988).
Budavari, Susan et al., "The Merck Index", An Encyclopedia of Chemical, Drugs, and Biologicals, 11th Ed., Merck & Co., Inc. (1989).
Papkoff, Jackie, Mol and Cell. Biol. 9(8):3377–3384 (1989).
Baba, Masanori et al., Proc. Natl. Acad. Sci. U.S.A. 85:6132–6136 (1988).
Sugawara, I. et al., Experientia 45:996–998 (1989).
Hammonds, R. Glenn, Jr., et al., Molecular Endocrinology 5(1):149–155 (1991).

*Primary Examiner*—George C. Elliott
*Attorney, Agent, or Firm*—Patricia A. McDaniels; Bruce M. Eisen

[57] ABSTRACT

An improved process for producing recombinant bone-inducing protein of the BMP-2 family as described. A suitable mammalian host cell transformed with a DNA encoding the protein is cultured in an appropriate culture medium to which is added about 10 to 1000 $\mu$g/ml dextran sulfate. The presence of dextran sulfate in the medium results in an increased yield of recombinant bone-inducing protein.

3 Claims, No Drawings

PRODUCTION OF RECOMBINANT BONE-INDUCING PROTEINS

This invention relates to a method for increasing the yield of recombinant bone-inducing proteins of the BMP-2 family.

BACKGROUND OF THE INVENTION

The cloning and expression of the recombinant osteogenic proteins of the BMP-2 family has previously been described (J.M. Wozny, et al., Science 242:1528–1534 (1988); E.A. Wang, et al., Proc. Natl. Acad. Sci. USA 87:2220–2224 (1990), incorporated herein by reference). Osteogenic proteins of the BMP-2 family are a promising development in the bone and cartilage field. The BMP-2 family of proteins includes BMP-3, BMP-4, BMP-5, BMP-6 and BMP-7, and bone-inducing proteins and proteins which are encoded by DNA sequences which hybridize thereto under stringent conditions. The DNA sequence of BMP-2 is shown in SEQ ID No:1.

These osteogenic proteins may be produced in cultured mammalian cell lines by transformation with an expression vector containing the respective cDNAs. The yield of expressed recombinant bone-inducing proteins can be increased in accordance with the present invention by addition of dextran sulfate to the cell culture medium.

DESCRIPTION OF THE INVENTION

Genes encoding the foregoing recombinant osteogenic proteins may be expressed in mammalian cell lines such as CHO (Chinese Hamster Ovary), COS, BHK, Balb/c 3T3, 293, and similar cell lines known in the art. The mammalian cells may be grown in any suitable medium, such as α-MEM, Dulbecco's MEM, RPMI 1640, and other media (Freshney, R.I., *Culture of Animal Cells, A Manual of Basic Technique*, Alan R. Liss, Inc., New York (1983)). The cells may be grown in the presence or absence of a serum supplement such as fetal bovine serum (FBS). The cells may be grown in monolayer or suspension culture, and additionally may be grown in large production scale batches The expressed osteogenic proteins are recovered from the culture medium and can be purified using known methods.

Transformed CHO cells are the preferred host cells used to produce an osteogenic protein of the BMP-2 family in accordance with the present invention. The cell growth medium may be supplemented with FBS to improve the growth of transformed CHO cells in culture. If it is desired to add FBS, concentrations of FBS as low as 0.5% (v/v) may be added. However, addition of animal-origin proteins always presents the risk of harboring viruses and other deleterious agents. The addition of FBS is not necessary for the practice of the present invention.

Any dextran sulfate may be used. One example is dextran sulfate of molecular weight 500,000 and sulfur content 17% (Pharmacia). Another example is dextran sulfate of molecular weight 5,000 and sulfur content 18% (Sigma catalogue #D-7037).

In accordance with the present invention, the growth medium is supplemented with dextran sulfate at a range of concentrations from about 1 to about 500 μg/mL. Higher concentrations of dextran sulfate work but may interfere with cell growth or protein purification. Preferably, the growth medium is supplemented with about 5 μg/ml to about 50 μg/ml dextran sulfate. Most preferably, the growth medium is supplemented with about 10 to 20 μg/ml dextran sulfate.

Expression of BMP-2 can be achieved by inserting a BMP-2 gene (SEQ ID NO:1) into an expression vector, inserting this vector into a mammalian cell, and selecting for cells which express BMP-2. See allowed commonly assigned, U.S. patent application Ser. No. 179,100, filed Apr. 8, 1988, now U.S. Pat. No. 5,013,649, the contents of which are incorporated herein by reference.

The yield of recombinant BMP-2 protein from mammalian cells which express the BMP-2 gene may be measured by known methods such as radioactively labeling cells with [$^{35}S$]- methionine and analyzing secreted proteins by polyacrylamide gel electrophoresis (PAGE) and autoradiography. For measurement of BMP-2 expression from production-scale batches, the amount of functional BMP-2 secreted is preferably quantitated by bioassay. Any appropriate bioassay may be used, for example, assay of induction of alkaline phosphatase activity in a BMP-2-responsive cell line, or assay of ectopic bone formation in a mammal such as rat, rabbit, cat or dog.

The optimal concentration of dextran sulfate for increasing yield of BMP-2 was determined by pulse labelling cells with [$^{35}S$]-methionine, followed by a four hour chase in varying amounts of dextran sulfate. Total secreted protein was then analyzed by PAGE and autoradiography. Cells were analyzed under two growth conditions: 1) standard adherent monolayers, and 2) suspension and serum free adapted cultures. Two different sizes of dextran sulfate (5000 dalton and 500,000 dalton) were tested for each growth condition. A concentration range of 1 μg/ml to 1000 μg/ml was examined for each size dextran sulfate on each growth state.

The results demonstrate that the potency of the 5000 dalton material was similar to the 500,000 dalton dextran sulfate for both monolayer and suspension cells. For cells grown in suspension, 1 μg/ml dextran sulfate produced a small increase in BMP-2 levels. Yield was near maximal at 10 μg/ml, and was approximately three-fold higher than in the absence of dextran sulfate. Increasing the dextran sulfate concentration to 100 μg/ml elicited a further 10% increase in BMP-2 yield. As another example, BMP-2 yield was about 40% higher utilizing 1000 μg/ml dextran sulfate than utilizing 10 μg/ml dextran sulfate. In other words 1000 μg/ml dextran sulfate yielded approximately four-fold more BMP-2 than was obtained in the absence of the compound.

While a similar graded response was observed with monolayer cells, the potency of dextran sulfate in increasing BMP-2 yield was reduced about 10-fold. Threshold effects were seen at 10 μg/ml, while levels of 100–300 μg/ml were needed to elicit a near-maximal response. Typically, 100 μg/ml dextran sulfate was used to increase the yield of BMP-2 from cells grown in monolayers. The magnitude of the dextran sulfate effect was about four-fold, similar to that seen with suspension cells.

The yield of the other osteogenic proteins, BMP-3, BMP-4, BMP5, BMP-6 and BMP-7, may similarly be improved with the addition of dextran sulfate to the cell culture medium.

I claim:

1. In a process for producing a recombinant bone-inducing protein of the BMP-2 family which comprises culturing in a suitable culture medium a mammalian host cell grown in suspension, said host cell being transformed with a DNA sequence encoding said protein as set forth in SEQ ID NO:1, and recovering the protein from said culture medium, the improvement for increasing the yield of said bone-inducing protein which comprises adding about 10 to about 1000 μμg/ml dextran sulfate to said culture medium.

2. The process of claim 1, wherein said amount of dextran sulfate is in the range of about 10 to 20 μg/ml.

3. In a process for producing a recombinant bone-inducing protein of the BMP-2 family which comprises culturing in a suitable culture medium a mammalian host cell grown in a monolayer, said host cell being transformed with a DNA sequence encoding said protein as set forth in SEQ ID NO:1, and recovering the protein from said culture medium, the improvement for increasing the yield of said bone-inducing protein which comprises adding about 100 to about 1000 μg/ml dextran sulfate to said culture medium.

* * * * *

UNITED STATES PATENT AND TRADEMARK OFFICE
CERTIFICATE OF CORRECTION

PATENT NO. : 5,318,898
DATED : June 7, 1994
INVENTOR(S) : Israel

It is certified that error appears in the above-indentified patent and that said Letters Patent is hereby corrected as shown below:

Column 1, line 45, replace "batches The" with --batches.  The--.

In claim 1, column 5, line 24, please replace "1000 µµg/ml" with --1000 µg/ml--

Signed and Sealed this

Twentieth Day of September, 1994

Attest:

Attesting Officer

BRUCE LEHMAN

Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
       ( A ) LENGTH: 1607 base pairs
       ( B ) TYPE: nucleic acid
       ( C ) STRANDEDNESS: single
       ( D ) TOPOLOGY: linear ( i i ) MOLECULE TYPE: cDNA ( v i ) ORIGINAL SOURCE:
       ( A ) ORGANISM: homo sapiens ( v i i ) IMMEDIATE SOURCE:
       ( B ) CLONE: HUMBMPII-CDNA-39

( i x ) FEATURE:
       ( A ) NAME/KEY: 5'UTR
       ( B ) LOCATION: 1..355

( i x ) FEATURE:
       ( A ) NAME/KEY: 3'UTR
       ( B ) LOCATION: 1544..1607

( x ) PUBLICATION INFORMATION:
       ( H ) DOCUMENT NUMBER: US 5,013,649
       ( I ) FILING DATE: 08-APR-1988
       ( J ) PUBLICATION DATE: 07-MAY-1991

( x i ) SEQUENCE DESCRIPTION: SEQ ID NO:1:

| | | | | | |
|---|---|---|---|---|---|
| GTCGACTCTA | GAGTGTGTGT | CAGCACTTGG | CTGGGGACTT | CTTGAACTTG | CAGGGAGAAT | 60 |
| AACTTGCGCA | CCCCACTTTG | CGCCGGTGCC | TTTGCCCCAG | CGGAGCCTGC | TTCGCCATCT | 120 |
| CCGAGCCCCA | CCGCCCCTCC | ACTCCTCGGC | CTTGCCCGAC | ACTGAGACGC | TGTTCCCAGC | 180 |
| GTGAAAAGAG | AGACTGCGCG | GCCGGCACCC | GGGAGAAGGA | GGAGGCAAAG | AAAAGGAACG | 240 |
| GACATTCGGT | CCTTGCGCCA | GGTCCTTTGA | CCAGAGTTTT | TCCATGTGGA | CGCTCTTTCA | 300 |
| ATGGACGTGT | CCCCGCGTGC | TTCTTAGACG | GACTGCGGTC | TCCTAAAGGT | CGACCATGGT | 360 |
| GGCCGGGACC | CGCTGTCTTC | TAGCGTTGCT | GCTTCCCCAG | GTCCTCCTGG | GCGGCGCGGC | 420 |
| TGGCCTCGTT | CCGGAGCTGG | GCCGCAGGAA | GTTCGCGGCG | GCGTCGTCGG | GCCGCCCCTC | 480 |
| ATCCCAGCCC | TCTGACGAGG | TCCTGAGCGA | GTTCGAGTTG | CGGCTGCTCA | GCATGTTCGG | 540 |
| CCTGAAACAG | AGACCCACCC | CCAGCAGGGA | CGCCGTGGTG | CCCCCCTACA | TGCTAGACCT | 600 |
| GTATCGCAGG | CACTCGGGTC | AGCCGGGCTC | ACCCGCCCCA | GACCACCGGT | TGGAGAGGGC | 660 |
| AGCCAGCCGA | GCCAACACTG | TGCGCAGCTT | CCACCATGAA | GAATCTTTGG | AAGAACTACC | 720 |
| AGAAACGAGT | GGGAAAACAA | CCCGGAGATT | CTTCTTTAAT | TTAAGTTCTA | TCCCCACGGA | 780 |
| GGAGTTTATC | ACCTCAGCAG | AGCTTCAGGT | TTTCCGAGAA | CAGATGCAAG | ATGCTTTAGG | 840 |
| AAACAATAGC | AGTTTCCATC | ACCGAATTAA | TATTTATGAA | ATCATAAAAC | CTGCAACAGC | 900 |
| CAACTCGAAA | TTCCCCGTGA | CCAGTCTTTT | GGACACCAGG | TTGGTGAATC | AGAATGCAAG | 960 |
| CAGGTGGGAA | AGTTTTGATG | TCACCCCCGC | TGTGATGCGG | TGGACTGCAC | AGGGACACGC | 1020 |
| CAACCATGGA | TTCGTGGTGG | AAGTGGCCCA | CTTGGAGGAG | AAACAAGGTG | TCTCCAAGAG | 1080 |
| ACATGTTAGG | ATAAGCAGGT | CTTTGCACCA | AGATGAACAC | AGCTGGTCAC | AGATAAGGCC | 1140 |
| ATTGCTAGTA | ACTTTTGGCC | ATGATGGAAA | AGGGCATCCT | CTCCACAAAA | GAGAAAAACG | 1200 |
| TCAAGCCAAA | CACAAACAGC | GGAAACGCCT | TAAGTCCAGC | TGTAAGAGAC | ACCCTTTGTA | 1260 |
| CGTGGACTTC | AGTGACGTGG | GGTGGAATGA | CTGGATTGTG | GCTCCCCCGG | GGTATCACGC | 1320 |

| | | | | | | |
|---|---|---|---|---|---|---|
| CTTTTACTGC | CACGGAGAAT | GCCCTTTTCC | TCTGGCTGAT | CATCTGAACT | CCACTAATCA | 1380 |
| TGCCATTGTT | CAGACGTTGG | TCAACTCTGT | TAACTCTAAG | ATTCCTAAGG | CATGCTGTGT | 1440 |
| CCCGACAGAA | CTCAGTGCTA | TCTCGATGCT | GTACCTTGAC | GAGAATGAAA | AGGTTGTATT | 1500 |
| AAAGAACTAT | CAGGACATGG | TTGTGGAGGG | TTGTGGGTGT | CGCTAGTACA | GCAAAATTAA | 1560 |
| ATACATAAAT | ATATATATAT | ATATATATTT | TAGAAAAAAG | AAAAAA | | 1607 |